(12) United States Patent
Hizaler Hoffmann et al.

(10) Patent No.: US 8,697,914 B2
(45) Date of Patent: Apr. 15, 2014

(54) PROCESS FOR PREPARING BIS(PARA-AMINOCYCLOHEXYL)METHANE

(75) Inventors: Evin Hizaler Hoffmann, Köln (DE); Leslaw Mleczko, Dormagen (DE); Ralph Schellen, Dormagen (DE); Stephan Schubert, League City, TX (US)

(73) Assignee: Bayer Intellectual Property GmbH, Monheim (DE)

( * ) Notice: Subject to any disclaimer, the term of this patent is extended or adjusted under 35 U.S.C. 154(b) by 106 days.

(21) Appl. No.: 13/139,707

(22) PCT Filed: Dec. 4, 2009

(86) PCT No.: PCT/EP2009/008669
§ 371 (c)(1),
(2), (4) Date: Jun. 14, 2011

(87) PCT Pub. No.: WO2010/069484
PCT Pub. Date: Jun. 24, 2010

(65) Prior Publication Data
US 2011/0251431 A1    Oct. 13, 2011

(30) Foreign Application Priority Data
Dec. 20, 2008  (DE) .................. 10 2008 064 280

(51) Int. Cl.
*C07C 209/00*    (2006.01)

(52) U.S. Cl.
USPC .......................................... 564/451

(58) Field of Classification Search
None
See application file for complete search history.

(56) References Cited

U.S. PATENT DOCUMENTS

| 3,347,917 | A | * | 10/1967 | Arthur ........................ 564/451 |
| 5,196,594 | A |  | 3/1993 | Schmelzer et al. |
| 6,998,507 | B1 |  | 2/2006 | Ding et al. |
| 2002/0183556 | A1 | * | 12/2002 | Tilling et al. ................ 564/451 |

FOREIGN PATENT DOCUMENTS

| EP | 1 251 951 B1 | 12/2004 |
| EP | 1 566 372 A1 | 8/2005 |
| WO | 01/54806 A1 | 8/2001 |

OTHER PUBLICATIONS

Ullmanns Encyclopedia of Industrial Chemistry (Fifth, Completely Revised Edition, vol. B4, p. 95-104, p. 210 216).
International Search Report Dated Mar. 17, 2010.

* cited by examiner

*Primary Examiner* — Clinton Brooks
(74) *Attorney, Agent, or Firm* — Norris McLaughlin & Marcus PA

(57) ABSTRACT

Process for preparing bis(para-amino-cyclohexyl)methane by multiphase reaction of methylenedianiline with hydrogen, in which the reaction is performed in 5 to 50 series-connected reaction zones under adiabatic conditions.

10 Claims, No Drawings

PROCESS FOR PREPARING BIS(PARA-AMINOCYCLOHEXYL)METHANE

This is a 371 of PCT/EP2009/008669, filed 4 Dec. 2009 (international filing date), which claims foreign priority benefit under 35 U.S.C. §119 of German Patent Application No. 10 2008 064 280.0 filed Dec. 20, 2008

BACKGROUND OF THE INVENTION

The present invention relates to a process for preparing bis(para-aminocyclohexyl)methane by multiphase reaction of methylenedianiline with hydrogen, in which the reaction is performed in 5 to 50 series-connected reaction zones under adiabatic conditions.

Bis(para-aminocyclohexyl)methane (PACM) is generally prepared under the catalytic influence of transition metal catalysts, for instance ruthenium catalysts or rhodium catalysts, from a liquid phase comprising methylenedianiline and a gaseous phase comprising hydrogen in an exothermic catalytic reaction according to Formula (I):

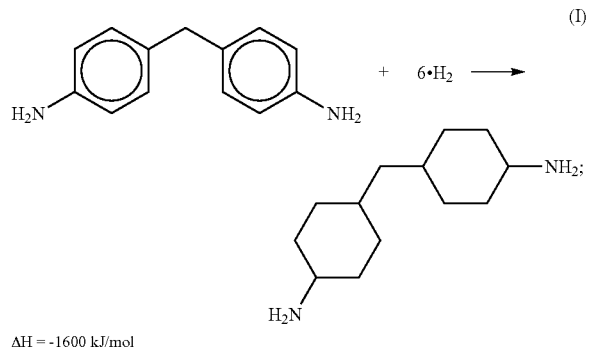

ΔH = -1600 kJ/mol

The PACM prepared by means of the reaction according to Formula (I) is an intermediate in the preparation of polyurethane, which in turn possesses a wide range of possible uses.

For instance, the resulting polyurethane finds use as a base for coatings. Alternatively, it can be foamed and thus used as polyurethane foam, for instance as an insulating material or as a cushioning material.

The reaction according to Formula (I) releases a considerable amount of heat which at first is absorbed in the liquid phase and has to be removed therefrom again in order to prevent, for instance, evaporation of the liquid phase. Moreover, the temperature of such reactions must be controlled in order to prevent the possibility of explosive side reactions, as known to the person skilled in the art in connection with aromatic chemistry.

U.S. Pat. No. 6,998,507 B1 discloses a process for preparing PACM, which also comprises the preparation of the methylenedianiline in a preliminary stage. The preparation of PACM according to the subject matter of this invention is performed in a reactor which comprises a monolithic catalyst in a stirred vessel. The catalyst is preferably a catalyst composed of a rhodium/ruthenium bimetallic catalyst.

The disclosure of U.S. Pat. No. 6,998,507 B1 does not include any indication to a possible adiabatic mode of operation of the reaction zone, although precooling of the methylenedianiline before entry into the reaction zone for preparing PACM is disclosed.

The process is disadvantageous because, in the case of failure of this only simple cooling provided according to U.S. Pat. No. 6,998,507 B1, the reaction runs away in an uncontrolled manner and the operating states with risk of explosion outlined above can be attained. Reliable and exact temperature control is, moreover, also not possible with the process disclosed in U.S. Pat. No. 6,998,507 B1 merely because considerable volumes of the reaction zone are not in direct contact with a heat-exchanging surface, such that the formation of uncontrolled temperature gradients within the reaction zone is probable, which probably also constitutes the reason for the essentially batchwise mode of operation according to the process of U.S. Pat. No. 6,998,507 B1.

A further process for general hydrogenations, including the hydrogenation of methylenedianiline to PACM according to the Formula (I) being considered here, is disclosed by EP 1 566 372 A1, which discloses trickle bed arrangements in tubes in the process disclosed here. The reaction zones which arise as a result may be filled with different catalyst materials. EP 1 566 372 further discloses that only upstream and/or downstream of a number of three series-connected reaction zones can cooling be effected.

There is no specific disclosure regarding an adiabatic or isothermal mode of operation in EP 1 566 372 A1. For the lack of a disclosure regarding thermal insulation around the reaction zones and in view of the high surface-to-volume ratio of the tube arrangement according to EP 1 566 372 A1, it can be assumed that it is desired to remove heat via the surfaces of the tubes, which leads, if anything, to a polytropic mode of operation of the process.

The process according to the disclosure of EP 1 566 372 A1 is disadvantageous, since, just as in the case of the process according to U.S. Pat. No. 6,998,507 B1, unsafe operating states of the strongly exothermic reaction according to the Formula (I) cannot be controlled sufficiently, since cooling of the reactants is provided only upstream and/or downstream of a multitude of reaction zones. Moreover, the heat of reaction, for the lack of measures for absorption thereof, is dissipated into the environment and is thus lost, which is uneconomic. A further factor associated with the lack of temperature control of the process according to EP 1 566 372 A1 is that the desired selectivities and yields of PACM can be complied with only with difficulty when there is operating disruption.

A third process for preparing PACM is disclosed by U.S. Pat. No. 5,196,594 A, according to which PACM among other substances can be formed from methylenedianiline with hydrogen in at least one fixed bed reactor at temperatures of 100° C. to 190° C. under a pressure of 50 to 350 bar.

The maximum number of reaction zones usable in series according to the disclosure of U.S. Pat. No. 5,196,594 A is two, and no cooling between the reaction zones is disclosed. Moreover, no specific disclosure regarding the mode of operation is given, from which a distinction between a preferably isothermal or adiabatic procedure could have been drawn.

The process according to U.S. Pat. No. 5,196,594 A has, however, at least the disadvantages of the processes according to the disclosures of EP 1 566 372 A1 and U.S. Pat. No. 6,998,507 B1, since sufficient temperature control cannot be achieved here either, which in turn leads at least to an endangerment potential or to insufficient yields/selectivities.

EP 1 251 951 (B1) discloses an apparatus and the possibility of performing chemical reactions in the apparatus, the apparatus being characterized by a cascade of reaction zones and heat exchanger apparatuses which are in contact with one another and are arranged cohesively bonded to one another in an integrated system. The process to be performed here is thus characterized by the contact of the different reaction zones with a particular heat exchanger apparatus in the form of a cascade.

There is no disclosure with regard to the usability of the apparatus and of the process for synthesis of PACM from liquid methylenedianiline and gaseous hydrogen. More particularly, applicability to polyphasic reaction systems in general is not disclosed.

It thus remains unclear how, proceeding from the disclosure of EP 1 251 951 (B1), such a reaction is to be performed by means of the apparatus and of the process performed therein. Moreover, for reasons of unity of invention, it has to be assumed that the process disclosed in EP 1 251 951 (B1) is performed in an apparatus identical or similar to the disclosure with regard to the apparatus. The result of this is that, due to the large-area contact of the heat exchange zones with the reaction zones according to the disclosure, a significant amount of heat is transferred by conduction of heat between the reaction zones and the adjacent heat exchange zones. The disclosure with regard to the oscillating temperature profile can thus only be understood such that the temperature peaks found here would be greater if this contact were not to exist. A further indication of this is the exponential rise in the temperature profiles disclosed between the individual temperature peaks. These indicate that a certain heat sink with notable but limited capacity is present in each reaction zone, which can reduce the temperature rise therein. It can never be ruled out that a certain removal of heat (for example by radiation) takes place; however, in the event of a reduction in the possible heat removal from the reaction zone, there would be an indication of a linear temperature profile or of one with declining slope, since no further metering of reactants is intended, and thus, after exothermic complete reaction, the reaction would become ever slower and the exothermicity generated would thus be reduced. Thus, EP 1 251 951 (B1) discloses multistage processes in cascades of reaction zones, from which heat is removed in an undefined amount by conduction of heat. Accordingly, the process disclosed is disadvantageous in that exact temperature control of the process gases of the reaction is impossible.

Proceeding from the prior art, it would therefore be advantageous to provide a process which can be performed in simple reaction apparatus and which enables exact, simple temperature control, such that it allows high conversions with maximum purities of the PACM product.

For the preparation of PACM from methylenedianiline by means of catalytic hydrogenation, as just described, no suitable processes capable of achieving the aforementioned objects in their entirety have been disclosed to date.

It is therefore an object of the invention to provide a process for catalytically hydrogenating methylenedianiline to PACM, which is performable with exact temperature control in simple reaction apparatus and which, as a result, allows high conversions at high purities of the product, the heat of reaction being utilizable either for the benefit of the reaction or in another way.

SUMMARY OF THE INVENTION

It has been found that, surprisingly, a process for preparing bis(para-aminocyclohexyl)methane (PACM) from methylenedianiline present in a liquid phase and hydrogen present in a process gas, in the presence of heterogeneous catalysts, characterized in that it is performed in 5 to 50 series-connected reaction zones in which the heterogeneous catalysts are present under adiabatic conditions, achieves this object.

DETAILED DESCRIPTION

In the context of the present invention, methylenedianiline refers to a liquid as a constituent of a liquid phase which is introduced into the process according to the invention and which comprises essentially methylenedianiline. Typically, the proportion of methylenedianiline in the liquid phase fed to the process is between 90 and 100% by weight, preferably between 95 and 100% by weight.

In the context of the present invention, hydrogen refers to a process gas which is introduced into the process according to the invention and which comprises essentially hydrogen. Typically, the proportion of hydrogen in the process gases fed to the process is between 90 and 100% by weight, preferably between 95 and 100% by weight.

In addition to the essential methylenedianiline component of the liquid phase, it may also comprise further secondary components. Nonexclusive examples of further secondary components which may be present in the liquid phase are, for instance, bis(para-aminocyclohexyl)methane, 4-(4'-aminobenzyl)cyclohexylamine, trans,trans-bis(para-aminocyclohexyl)methane, and also dissolved constituents of process gas.

In addition to the essential hydrogen component of the process gas, it may also comprise secondary components. Nonexclusive examples of secondary components which may be present in the process gas are, for instance, argon, nitrogen and/or carbon dioxide.

In general, in the context of the present invention, a process gas is understood to mean a gas mixture which comprises essentially hydrogen and secondary components, whereas a liquid phase is understood to mean a liquid and/or mixture of liquids and/or to mean a solution which comprises methylenedianiline and further secondary components.

"Essentially" thus means, according to the above definition, that a proportion of the essential component of the liquid phase and/or of the process gas of more than 90% by weight is present.

According to the invention, the performance of the process under adiabatic conditions means that essentially no heat is supplied actively to, nor is heat withdrawn from, the reaction zone from outside. It is common knowledge that complete insulation against supply or removal of heat is possible only by complete evacuation with exclusion of the possibility of heat transfer by radiation. "Adiabatically" in the context of the present invention therefore means that no measures are taken to supply or remove heat.

In an alternative embodiment of the process according to the invention, however, heat transfer can be reduced for example by insulation by means of commonly known insulators, for example polystyrene insulating materials, or else by sufficiently great distances from heat sinks or heat sources, in which case the insulator is air.

One advantage of the inventive adiabatic mode of operation with 5 to 50 series-connected reaction zones over a non-adiabatic mode of operation is that there is no need to provide any means of heat removal in the reaction zones, which implies a considerable simplification of the construction. This gives rise more particularly to simplifications in the manufacture of the reactor and in the scalability of the process, and a rise in the reaction conversions. Moreover, the heat generated in the course of progression of the exothermic reaction can be utilized in a controlled manner to enhance the conversion in the individual reaction zone.

A further advantage of the process according to the invention is the possibility of very exact temperature control, through the close graduation of adiabatic reaction zones. It is thus possible in each reaction zone to set and control a temperature which is advantageous in the progression of the reaction.

The catalysts used in the process according to the invention are typically catalysts which consist of a material which, in addition to its catalytic activity for the reaction according to Formula (I), is characterized by sufficient chemical resistance under the conditions of the process, and by a high specific surface area.

Catalyst materials which are characterized by such a chemical resistance under the conditions of the process are, for example, catalysts comprising ruthenium and/or rhenium and/or rhodium.

Usually, these materials are applied to supports which comprise oxides of aluminium and/or titanium and/or silicon.

In the context of the present invention, specific surface area refers to the area of the catalyst material which can be reached by the process gas, based on the mass of catalyst material used.

A high specific surface area is a specific surface area of at least 10 m$^2$/g, preferably of at least 20 m$^2$/g.

The inventive catalysts are present in the reaction zones in each case and may be present in all manifestations known per se, for example fixed bed and moving bed.

The manifestation as a fixed bed is preferred for the process according to the invention.

The fixed bed arrangement comprises a catalyst bed in the actual sense, i.e. loose, supported or unsupported catalyst in any form and in the form of suitable packings. The term "catalyst bed" as used here also encompasses continuous regions of suitable packings on a support material or structured catalyst supports. These would be, for example, ceramic honeycomb supports which are to be coated and have comparatively high geometric surface areas or corrugated layers of metal wire mesh on which, for example, catalyst granules are immobilized. In the context of the present invention, a special form of packing is considered to be the presence of the catalyst in monolithic form.

Where a fixed bed arrangement of the catalyst is used, the catalyst is present preferably in beds of particles with mean particle sizes of 1 to 10 mm, preferably 1.5 to 8 mm, more preferably of 2 to 6 mm.

When a moving bed arrangement of the catalyst is used, the catalyst is preferably present in loose beds of particles, as have already been described in connection with the fixed bed arrangement.

Beds of such particles are advantageous because the particles possess a high specific surface area of the catalyst material with respect to the liquid phase, i.e. the process gas, and hence a high conversion rate can be achieved. The mass transfer limitation of the reaction as a result of diffusion can thus be minimized. At the same time, the particles, though, are still not sufficiently small as to result in a disproportionate increase in pressure drops in the course of flow through the fixed bed. The ranges of the particle sizes specified in the preferred embodiment of the process, comprising a reaction in a fixed bed, are thus an optimum between the achievable conversion from the reaction according to Formula (I) and the pressure drop obtained in the course of performance of the process. Pressure drop is directly coupled to the energy needed in the form of pump and/or compressor output, such that a disproportionate increase therein would result in an uneconomic mode of operation of the process.

In a preferred embodiment of the process according to the invention, the conversion is effected in 10 to 40 and more preferably 15 to 35 series-connected reaction zones.

A preferred further embodiment of the process is characterized in that the process gas leaving at least one reaction zone and the liquid phase are subsequently passed through at least one heat exchange zone connected downstream of this reaction zone.

In a particularly preferred further embodiment of the process, downstream of each reaction zone is at least one, preferably one, heat exchange zone through which the process gas leaving the reaction zone and liquid phase are passed.

The reaction zones may either be arranged in one reactor or be arranged divided between a plurality of reactors. The arrangement of the reaction zones in one reactor leads to a reduction in the number of apparatuses used.

The individual reaction zones and heat exchange zones can also be arranged together in one reactor or in any desired combinations of in each case reaction zones with heat exchange zones divided between a plurality of reactors.

When reaction zones and heat exchange zones are present in one reactor, in an alternative embodiment of the invention, a thermal insulation zone is present between them, in order to be able to obtain the adiabatic operation of the reaction zone.

In addition, individual series-connected reaction zones may independently also be replaced or supplemented by one or more parallel-connected reaction zones. The use of parallel-connected reaction zones allows, more particularly, the exchange or addition thereof with running continuous overall operation of the process.

Parallel- and series-connected reaction zones can especially also be combined with one another. More preferably, the process according to the invention, however, has exclusively series-connected reaction zones.

The reactors used with preference in the process according to the invention may consist of simple vessels with one or more reaction zones, as described, for example, in Ullmanns Encyclopedia of Industrial Chemistry (Fifth, Completely Revised Edition, Vol. B4, page 95-104, page 210-216), in which case thermal insulation zones may additionally be provided between each of the individual reaction zones and/or heat exchange zones.

In an alternative embodiment of the process, there is thus at least one thermal insulation zone between a reaction zone and a heat exchange zone. There is preferably a thermal insulation zone around each reaction zone.

The catalysts or the fixed beds thereof are installed in a manner known per se on or between gas- and liquid-permeable walls comprising the reaction zone of the reactor. Especially in the case of thin fixed beds, technical devices for homogeneous gas and/or liquid distribution may be installed upstream of the catalyst beds in flow direction. These may be perforated sheets, bubble-cap trays, valve trays or other internals, which bring about homogeneous entry of the process gas and/or of the liquid phase into the fixed bed by generating a small but homogeneous pressure drop.

In a preferred embodiment of the process, the inlet temperature of the liquid phase entering the first reaction zone is from 10 to 170° C., preferably from 50 to 150° C., more preferably from 90 to 140° C.

The temperature of the liquid phase is important, since this, measured relative to the process gas, has a heat capacity several orders of magnitude higher, such that it adjusts the process gas, which may be warmer or colder, to approximately the same temperature within a short time in the reaction zone. More preferably, however, the process gas likewise has the aforementioned temperature on entry into the particular reaction zone.

In a further preferred embodiment of the process, the absolute pressure at the inlet of the first reaction zone is more than 5 bar, preferably between 10 and 200 bar, more preferably between 20 and 160 bar.

In yet a further preferred embodiment of the process, the residence time of the process gas and of the liquid phase in all reaction zones together is between 1 and 100 s, preferably between 2 and 80 s, more preferably between 5 and 50 s.

The liquid phase and the process gas are preferably fed in only upstream of the first reaction zone. This has the advantage that the entire liquid phase can be utilized for the absorption and removal of the heat of reaction in all reaction zones. Moreover, such a procedure can enhance the space-time yield, or decrease the catalyst mass needed. However, it is also possible if required to meter in liquid phase comprising methylenedianiline, preferably pure liquid methylenedianiline, upstream of one or more of the reaction zones which follow downstream of the first reaction zone. The supply of liquid phase between the reaction zones additionally allows the temperature of the conversion to be controlled.

In a preferred embodiment of the process according to the invention, the liquid phase and the process gas are cooled downstream of at least one of the reaction zones used, more preferably downstream of each reaction zone.

To this end, the liquid phase and the process gas, after leaving a reaction zone, are conducted through one or more of the abovementioned heat exchange zones which are connected downstream of the particular reaction zones. These may be configured as heat exchange zones in the form of the heat exchangers known to those skilled in the art, for example tube bundle heat exchangers, plate heat exchangers, annular groove heat exchangers, spiral heat exchangers, fin-tube heat exchangers and/or microstructured heat exchangers. The heat exchangers are preferably micro-structured heat exchangers.

In the context of the present invention, "microstructured" means that the heat exchanger, for the purpose of heat transfer, comprises fluid-conducting channels which are characterized in that they have a hydraulic diameter between 50 μm and 5 mm. The hydraulic diameter is calculated from four times the flow cross-sectional area of the fluid-conducting channel divided by the circumference of the channel.

In a particular embodiment of the process, as the liquid phase and the process gas are cooled in the heat exchange zones by the heat exchanger, steam is raised.

Within this particular embodiment, it is preferred to perform an evaporation, preferably partial evaporation, in the heat exchangers which contain the heat exchange zones, on the side of the cooling medium.

In the context of the present invention, "partial evaporation" means an evaporation in which a gas/liquid mixture of a substance is used as a cooling medium and in which a gas/liquid mixture of a substance is also still present after heat transfer in the heat exchanger.

The performance of an evaporation is particularly advantageous because, as a result, the achievable heat transfer coefficients of/to process gases and liquid phase to/from cooling/heating media become particularly high, thus allowing efficient cooling to be achieved.

The performance of a partial evaporation is particularly advantageous because the absorption/release of heat by the cooling medium, as a result, no longer results in a temperature change of the cooling medium, but the gas/liquid equilibrium is merely shifted. The consequence of this is that the liquid phase and the process gas are cooled against a constant temperature over the entire heat exchange zone. This in turn reliably prevents the occurrence of radial temperature profiles in the flow of liquid phase and/or process gases, which improves the control over the reaction temperatures in the reaction zones and especially prevents the development of local overheating as a result of radial temperature profiles.

In an alternative embodiment, instead of an evaporation/partial evaporation, it is also possible to provide a mixing zone upstream of the inlet of a reaction zone, in order to homogenize any radial temperature profiles which arise in the course of cooling in the flow of liquid phase and/or process gases by mixing transverse to the main flow direction.

In a preferred embodiment of the process, the reaction zones connected in series are operated at an average temperature rising or falling from reaction zone to reaction zone. This means that, within a sequence of reaction zones, the temperature can be allowed either to rise or fall from reaction zone to reaction zone. This can be established, for example, via the control of the heat exchange zones connected between the reaction zones. Further means of adjusting the average temperature are described hereinafter.

The thickness of the reaction zones through which the flow proceeds may be selected identically or differently, and is calculated according to laws which are common knowledge to those skilled in the art from the above-described residence time and the particular amounts of liquid phase and process gas throughput in the process.

The mass flow throughputs of liquid phase comprising the process product (PACM) which are passable by the process in accordance with the invention, from which the amounts of methylene-dianiline to be used are also calculated, are typically between 0.01 and 30 t/h, preferably between 0.1 and 20 t/h, more preferably between 1 and 15 t/h.

The maximum exit temperature of liquid phase and/or process gases from the reaction zones is typically within a range from 130° C. to 250° C., preferably from 140° C. to 230° C., more preferably from 150° C. to 210° C. The temperature in the reaction zones is preferably controlled by at least one of the following measures: selecting the dimensions of the adiabatic reaction zone, controlling the heat removal between the reaction zones, adding liquid phase between the reaction zones, molar ratio of the reactants/excess of hydrogen used, addition of inert gases, especially nitrogen, carbon dioxide, upstream of and/or between the reaction zones.

The composition of the catalysts in the inventive reaction zones may be the same or different. In a preferred embodiment, the same catalysts are used in each reaction zone. However, it is also possible advantageously to use different catalysts in the individual reaction zones. For instance, especially in the first reaction zone, when the concentration of the reactants is still high, a less active catalyst can be used, and, in the further reaction zones, the activity of the catalyst can be increased from reaction zone to reaction zone. The catalyst activity can also be controlled by dilution with inert materials or support material. It is likewise advantageous, especially in the first and/or second reaction zone, to use a catalyst which is particularly stable to deactivation at the temperatures of the process in these reaction zones.

The process according to the invention can prepare, per 1 kg of catalyst, 0.1 kg/h to 50 kg/h, preferably 1 kg/h to 20 kg/h, more preferably 2 kg/h to 10 kg/h, of PACM.

The process according to the invention is thus notable for high space-time yields, associated with a reduction in the apparatus sizes and a simplification of the apparatuses or reactors. This surprisingly high space-time yield is enabled by the interplay of the inventive and preferred embodiments of the novel process. Especially the interplay of graduated adiabatic reaction zones with heat exchange zones in-between and the defined residence times enables exact control of the process and the resulting high space-time yields, and also a reduction in the risk of operating states with explosion hazards, and the simplification of the process, since no catalyst removal and recycling are required.

The invention claimed is:

1. Process for preparing bis(para-aminocyclohexyl)methane (PACM) from methylenedianiline present in a liquid phase and hydrogen present in a process gas, in the presence of heterogeneous catalysts, performed in 5 to 50 series-connected reaction zones in which the heterogeneous catalysts are present in fixed bed arrangement, under adiabatic conditions.

2. Process according to claim 1, wherein the conversion is accomplished in 10 to 40 series-connected reaction zones.

3. Process according to claim 1 wherein the inlet temperature of the liquid phase entering the first reaction zone is from 10 to 170° C.

4. Process according to claim 1, wherein the absolute pressure at the inlet of the first reaction zone is more than 5 bar.

5. Process according to claim 1, wherein the residence time of the process gas and of the liquid phase in all reaction zones together is between 1 and 100 s.

6. Process according to claim 1, wherein the catalysts are present in beds of particles with mean particle sizes of 1 to 10 mm.

7. Process according to claim 1, wherein, downstream of at least one reaction zone there is at least one heat exchange zone through which the process gas and the liquid phase are passed.

8. Process according to claim 7, wherein, downstream of each reaction zone there is at least one heat exchange zone through which the process gas and liquid phase are passed.

9. Process according to claim 1, wherein, between a reaction zone and a heat exchange zone there is at least one thermal insulation zone.

10. Process according to claim 9, wherein there is a thermal insulation zone around each reaction zone.

* * * * *